United States Patent [19]
Garrou et al.

[11] 4,149,274
[45] Apr. 17, 1979

[54] ANTI-SLIP HOSIERY ARTICLE AND METHOD

[75] Inventors: Louis W. Garrou; Daniel B. Bounous; Russell L. Huffman, all of Valdese, N.C.

[73] Assignee: Alba-Waldensian, Incorporated, Valdese, N.C.

[21] Appl. No.: 950,133

[22] Filed: Oct. 10, 1978

[51] Int. Cl.² .................. A41B 11/02; A61F 13/08
[52] U.S. Cl. .................................... 2/239; 2/83; 66/185
[58] Field of Search ............... 2/239, 241, 61, 80, 2/83, 243 R; 66/185, 186, 187, 172 E

[56] References Cited

U.S. PATENT DOCUMENTS

| | | | |
|---|---|---|---|
| 2,050,535 | 8/1936 | Martel | 66/185 X |
| 2,102,368 | 12/1937 | Martel | 66/185 X |
| 2,746,054 | 5/1956 | Heilbronner | 2/83 |
| 4,069,515 | 1/1978 | Swallow et al. | 2/239 |

*Primary Examiner*—H. Hampton Hunter
*Attorney, Agent, or Firm*—Bell, Seltzer, Park & Gibson

[57] ABSTRACT

The present hosiery article includes an anti-slip lower sole portion formed with outwardly extending loops of yarn having a high coefficient of friction, such as bare spandex, which is integrally knit with the body yarn during the knitting of the foot portion of the hosiery article. The loops of friction yarn on the outer surface of the sole portion engage the floor and minimize slippage of the foot of the wearer. This hosiery article is particularly adapted for use by bed patients and the formation of the loops of friction yarn does not unduly restrict the contraction and stretchability of the hosiery article.

23 Claims, 6 Drawing Figures

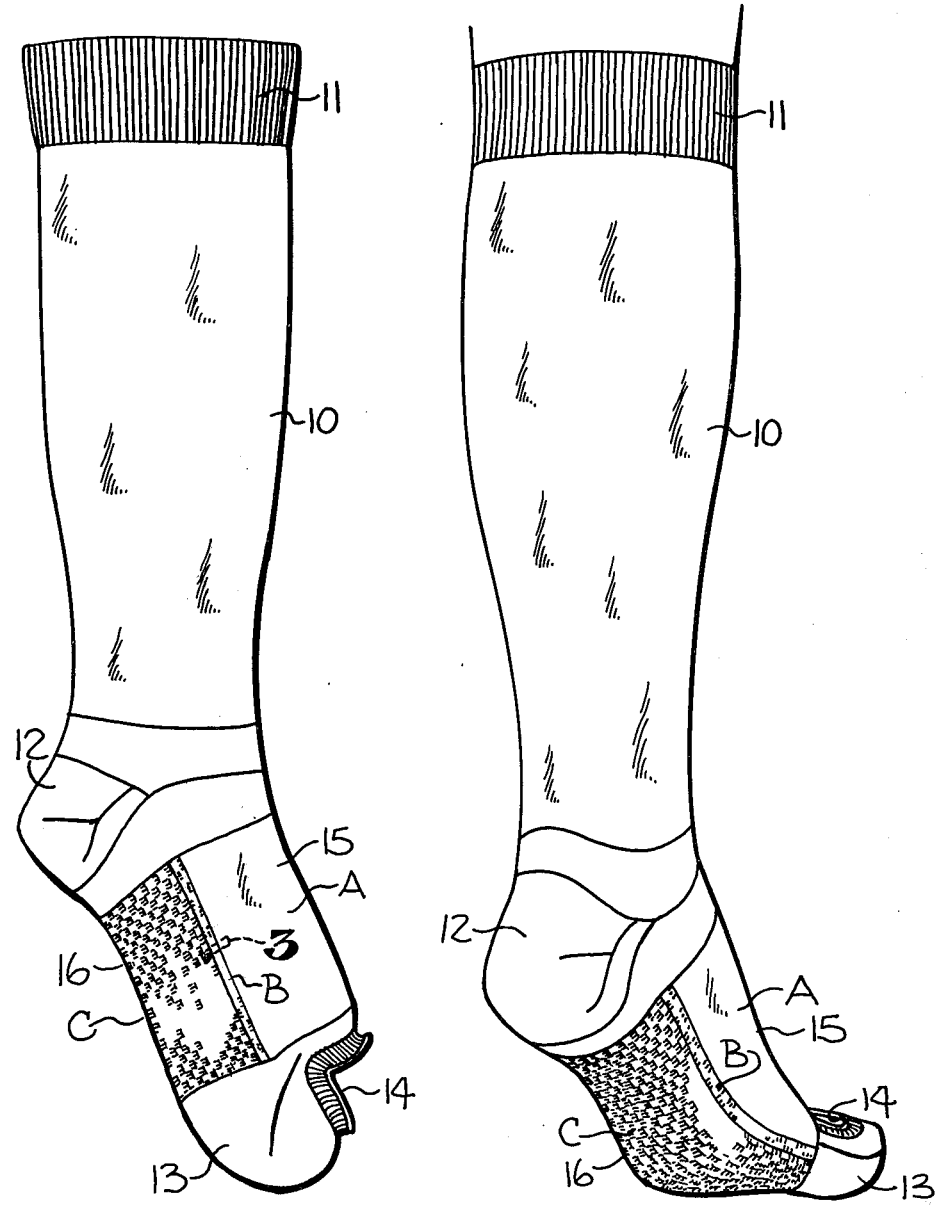

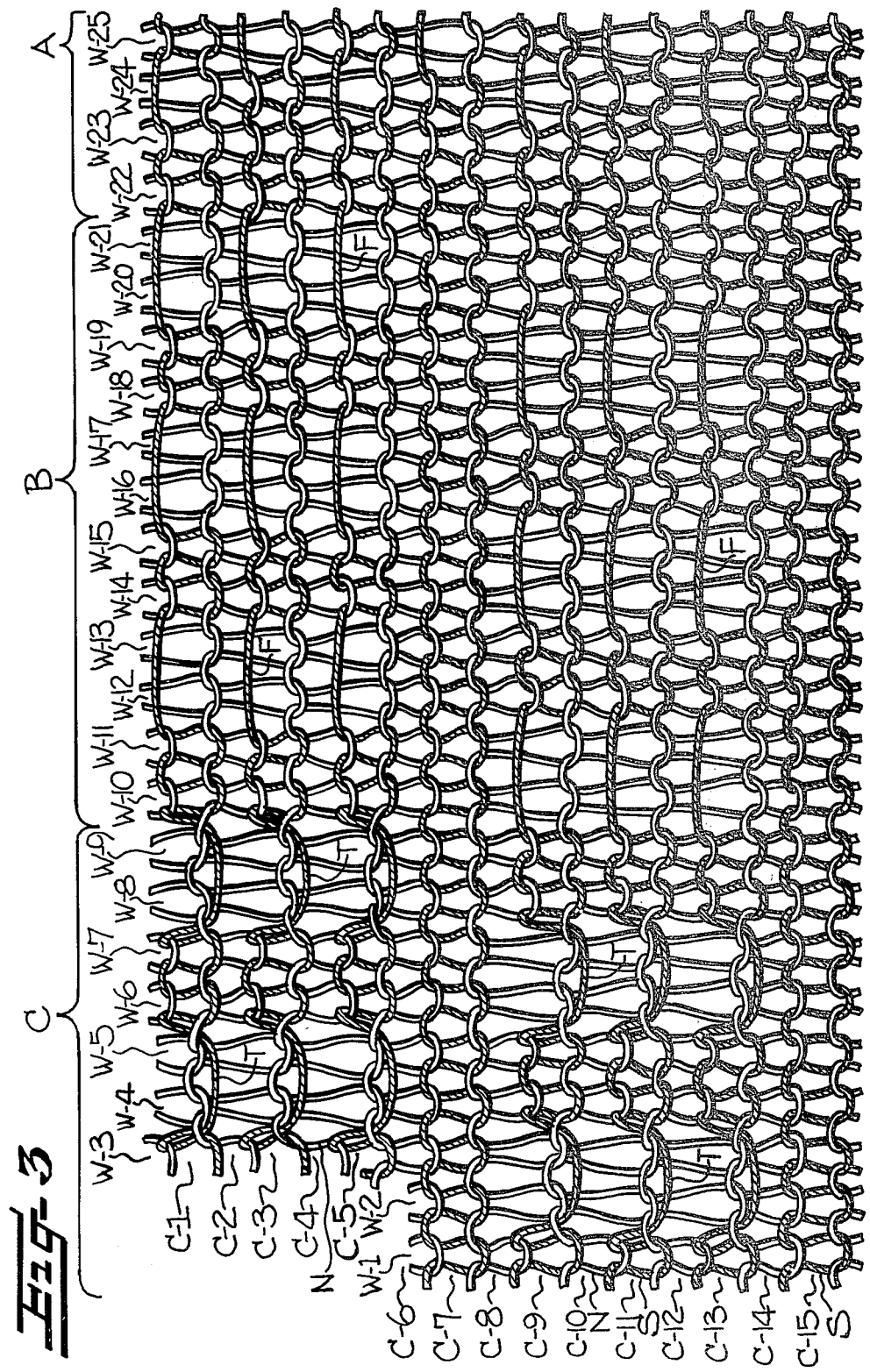

ANTI-SLIP HOSIERY ARTICLE AND METHOD

FIELD OF THE INVENTION

This invention relates to hosiery articles for use primarily by bed patients and includes friction yarn knit in the sole portion and forming loops or floats extending outwardly therefrom to engage the floor and minimize slippage of the foot of the patient.

BACKGROUND OF THE INVENTION

It is a common practice for bed patients to wear therapeutic or anti-embolism stockings, particularly when confined to the bed after an operation, to reduce the likelihood of thromboembolism. Also, it may be desirable for bed patients to wear other types of hosiery articles, such as low-cut slipper type socks to aid in maintaining the feet of the patient warm. When a bed patient wearing a hosiery article leaves the bed and attempts to walk on the adjacent floor, the patient may slip and fall causing serious bodily injury. While most patients are warned to put on slippers or shoes when leaving the bed, many patients ignore these instructions and walk on the floor with the hosiery article directly thereagainst.

The desirability of providing some type of anti-slip or non-slip surface on the sole of an anti-embolism stocking has been recognized in U.S. Pat. No. 4,021,860. This patent discloses the use of an inelastic strip or sheet of non-slip material attached to the lower sole portion of the stocking. In accordance with this patent, the non-slip material is fused or adhered to the sole of the stocking while in a stretched condition so that the elasticity of the stocking is not unduly restricted. However, since the strip or sheet of non-slip material is inelastic, the non-slip material does limit the contraction and may somewhat limit the stretchability of the sole portion of the stocking to which it is fused or otherwise attached. Also, the attachment of the inelastic strip or sheet of non-slip material requires a separate operation and thereby adds to the cost of producing the stocking. The non-slip strips make the corresponding portions of the stockings stiff and may also distract from the normally uniform appearance of the stocking.

SUMMARY OF THE INVENTION

With the foregoing in mind, it is an object of the present invention to provide a hosiery article for use primarily by bed patients with anti-slip means on the outer surface of the sole portion to engage the floor and minimize slippage of the foot of the patient and wherein the anti-slip means is formed as an integral part of the hosiery article and during the knitting of the hosiery article to eliminate a separate attaching operation.

It is another object of the present invention to provide such a hosiery article wherein the incorporation of the anti-slip means does not limit the stretchability, contraction and flexibility of the hosiery article and does not distract from its appearance.

In accordance with the present invention, the anti-slip means is provided on the outer surface of the sole portion of the hosiery article and extends throughout a substantial portion thereof to provide a relatively high frictional surface so as to minimize slippage of the foot of the patient on the floor. The anti-slip means comprises friction yarn having a substantially higher coefficient of friction than the body yarn of which the hosiery article is knit and the friction yarn is interknit with the body yarn in spaced-apart areas of the sole portion. The friction yarn forms unknit portions on the outer surface of the sole portion with the unknit portions providing loops or floats extending between the spaced-apart areas in which the friction yarn is interknit with the body yarn. The loops or floats of the friction yarn engage the floor and minimize slippage of the foot of the patient. The friction yarn is also stretchable, such as a bare uncovered spandex yarn so that the incorporation of the friction yarn in the sole portion of the hosiery article does not unduly limit the contraction and stretchability of the hosiery article and does not unduly distract from the appearance thereof. The unknit portions of the spandex yarn on the outer surface of the sole portion may be formed by tucking or floating the spandex yarn over several wales during the knitting of the foot portion of the hosiery article.

The anti-slip means in accordance with the present invention may be incorporated in the sole portion of various types of hosiery articles and is illustrated in one embodiment as being incorporated in one manner in the sole of a knee-high anti-embolism or therapeutic type stocking and is illustrated in another embodiment as being incorporated in another manner in the sole portion of a low-cut slipper type sock.

BRIEF DESCRIPTION OF THE DRAWINGS

Other objects and advantages will appear as the description proceeds when taken in connection with the accompanying drawings, in which FIG. 1 is a side elevational view of a knee-high type anti-embolism or therapeutic stocking with the present anti-slip means being incorporated in the sole portion thereof;

FIG. 2 is a perspective view of the sock of FIG. 1, illustrating its appearance when placed on the foot and leg of the wearer;

FIG. 3 is a greatly enlarged fragmentary view of the small area of the foot of the sock enclosed by the dotted rectangle 3 in FIG. 1 and illustrating the fabric in highly stretched condition;

DESCRIPTION OF THE ILLUSTRATED EMBODIMENTS

Figures 4, 5:
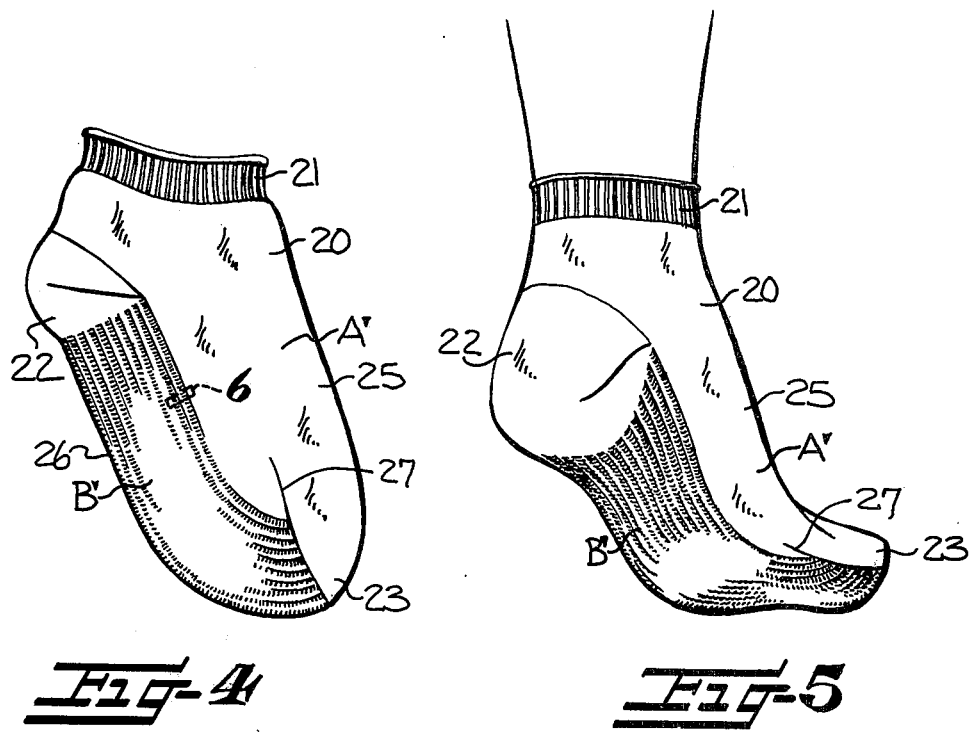
FIG. 4 is a side elevational view of a low-cut slipper type sock illustrating the present anti-slip means incorporated in the sole and lower portion of the toe closure thereof.
FIG. 5 is a perspective view of the sock of FIG. 4, illustrating its appearance when placed on the foot of the wearer.

Generally, each illustrated embodiment (FIGS. 1–3 and 4–6) of the anti-slip hosiery article in accordance with the present invention, is formed by knitting body yarn to form a leg and foot portion. While the foot portion is being knit, a friction yarn with a substantially higher coefficient of friction than the body yarn is interknit with the body yarn in spaced-apart areas of a substantial portion of the sole and forms unknit portions on the inner surface of the sole. The unknit portions extend between the spaced-apart areas in which the friction yarn is interknit with the body yarn and form loops or floats extending across a plurality of wales. During the knitting of the hosiery article, the loops or floats are formed on the inside of the sole portion. To position the unknit loops or floats of the friction yarn on the outer surface of the sole, the hosiery article is simply everted, following the knitting operation so that the hosiery article is worn in what is normally considered a "wrong-side-out" condition.

The hosiery article in FIGS. 1 and 2 is illustrated as an anti-embolism or therapeutic type knee-high stocking and includes a leg portion 10 which is illustrated as extending upwardly to a point just below the knee of the wearer with a turned welt cuff 11 formed integral with the upper end thereof. However, it is to be understood that the stocking may extend up to and cover the thigh of the patient or may also extend to the waist of the patient. The foot portion of the stocking is formed integral with the lower end of the leg 10 and includes a heel pocket 12 and a toe pocket 13 which is provided with a toe inspection opening 14. The portion of the foot between the heel pocket 12 and the toe pocket 13 is circumferentially divided into an upper instep portion 15 and a lower sole portion 16. The leg portion 10 is knit in a conventional manner with a textured stretchable body yarn, such as nylon, with an elastic or spandex yarn interknit therewith to provide a compressive force on the leg of the wearer and the compressive force is usually decreased in a gradual manner from the ankle upwardly.

As best illustrated in FIG. 3, the anti-slip means on the outer surface of the sole 16 is provided by interknitting a friction yarn, such as an uncovered spandex indicated at S, with a body yarn N in spaced-apart areas to form unknit portions in the form of loops or floats extending between the spaced-apart areas in which the friction yarn is interknit with the body yarn. The spandex yarn S is striped for ease of identification in FIG. 3 and is knit in alternate courses (the odd numbered courses) while the body yarn N is knit in intervening courses (the even numbered courses). In the upper instep portion 15, illustrated in the bracketed section A (wales W-22 through W-25), the spandex yarn S is alternately knit and floated in single wales and the wales in which the single wale floats appear are staggered walewise from course to course of the spandex yarn. The body yarn N is knit in plain stitch loops in every wale of each of the even numbered courses.

In the relatively narrow sections B, indicated by the bracketed wales W-10 through W-21 of FIG. 3, the spandex yarn S is knit in plain stitches in pairs of adjacent wales (wales W-10, W-11, W-14, W-15, W-18 and W-19 of courses C-1, C-3 and C-5) and forms floats F extending across pairs of adjacent wales (wales W-12, W-13, W-16, W-17, W-20 and W-21). The floats F formed in three successive courses of the spandex yarn (courses C-1, C-3 and C-5) are aligned in a walewise direction. The spandex yarn S is then knit in plain stitch loops in every wale in course C-7. The spandex yarn S again forms floats F extending across pairs of adjacent wales (wales W-10, W-11, W-14, W-15, W-18 and W-19) in the next three successive spandex courses (C-9, C-11 and C-13) so that these floats F are offset walewise relative to the floats F formed in the courses C-1, C-3 and C-5.

Throughout the remainder of the lower sole portion 16, as illustrated in the bracketed section C of FIG. 3 (wales W-1 through W-9), the spandex yarn S forms tuck loops T in adjacent pairs of wales (W-4, W-5, W-8, W-9) while forming plain stitch loops in the intervening pairs of wales (wales W-6 and W-7) of three consecutive spandex courses (C-1, C-3 and C-5). In course C-7, the spandex yarn S again knits plain stitch loops in every wale. In courses C-9, C-11 and C-13, the spandex yarn S forms tuck loops T in pairs of adjacent wales (W-2, W-3, W-6 and W-7) which are staggered walewise relative to the tuck loops T formed in the previous courses (C-1, C-3 and C-5).

When the foot portion is being knit on the circular hosiery knitting machine, the floats F and tuck loops T of the spandex yarn are formed on the inner surface of the sole portion 16 and are subsequently positioned on the outer surface of the sole portion by simply everting the hosiery article after it is removed from the knitting machine. Thus, the spandex yarn S is interknit in plain stitch loops with the body yarn N in pairs of adjacent wales and forms unknit portions extending between the spaced-apart areas in which the spandex yarn is interknit with the body yarn with the unknit portions of the spandex yarn forming tuck loops positioned on the outer surface of the sole portion 16 so as to engage the floor and minimize slippage of the foot of the patient.

The embodiment of the hosiery article in FIGS. 4 and 5 is illustrated as a low-cut slipper type sock and includes a short leg portion 20 with a cuff 21 at the upper end which is adapted to encircle and engage the ankle of the wearer. The foot portion includes a heel pocket 22 and a "fish mouth" type toe closure 23. The foot portion extending between the heel pocket 22 and the toe closure 23 is circumferentially divided into an upper instep portion 25 and a lower instep portion 26.

The fish mouth type toe closure 23 is formed in a well-known manner by a curved seam 27 extending around the toes of the wearer and this type of toe closure eliminates the need for forming a toe pocket by reciprocation. This type of toe construction also results in the unknit portions of the friction yarn in the lower sole portion 26 extending throughout the lower surface of the lower portion of the toe closure 23, in a manner to be presently described.

The leg portion 20 of the sock may be formed of a stretchable synthetic textured body yarn, such as nylon. The leg portion 20 is very short and may incorporate an elastic or spandex yarn therein to provide added stretchability and some compressive force against the ankle of the wearer. The cuff 21 may be knit in the well-known mock rib construction to aid in supporting the sock around the ankle.

Figure 6:
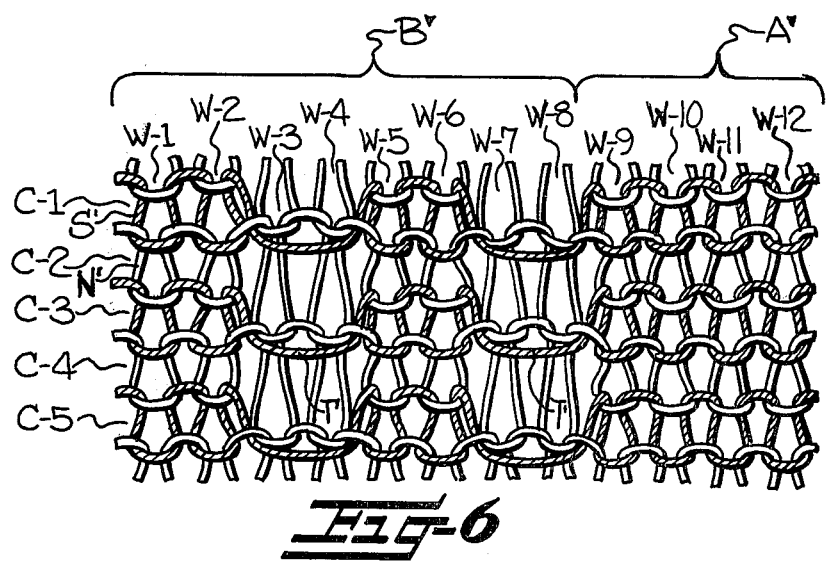
FIG. 6 is a greatly enlarged fragmentary view of the small area of the sock enclosed by the dotted rectangle 6 in FIG. 4 and illustrating the fabric in highly stretched condition.

As illustrated in FIG. 6, the spandex yarn S' is knit in plain stitch loops in every wale of the odd numbered courses throughout the upper instep portion 25, as indicated by the bracketed section A' encompassing wales W-9 through W-12. The stretchable nylon body yarn N' is knit in plain stitch loops in every wale of the even numbered courses throughout both the instep 25 and sole 26 of the foot portion.

In the lower sole area 26 (the bracketed section B' of FIG. 6), the spandex yarn S' is knit in the odd numbered courses and forms plain stitch loops in adjacent pairs of wales (W-1, W-2 and W-5, W-6) while forming tuck loops T' in pairs of adjacent wales (W-3, W-4 and W-7, W-8). The tuck loops T' are formed during the knitting of the lower sole portion 26 and are formed on the inside of the fabric while the sock is being knit. The fish mouth type of toe closure 23 is formed as straight tubular fabric on the knitting machine and the curved seam 27 is formed subsequent to the knitting operation. The seam 27 is preferably of the overedge type and is formed while the sock is in the "right-side-out" condition with the unknit loops of spandex yarn on the inside of the sock. After knitting and toe closing, the sock is everted so that it will be worn in the "wrong-side-out" condition with the unknit loops of spandex yarn on the outer surface of the sole 26 and the bulk of the seam 27 will be positioned inside of the sock. By using this type of toe closure, the unknit loops of the spandex yarn extend throughout the lower outer surface of the lower portion of the fish mouth type toe closure 23.

Thus, the unknit floats, tucks or loose loops of spandex yarn on the outer surface of the sole portion of each embodiment of the hosiery article are positioned to engage the floor and minimize slippage of the foot of the patient. Since the spandex yarn is also stretchable, the construction of the unknit loops on the outer surface of the sole portion does not restrict the contraction and stretchability of the hosiery article. Also, the knitting of the spandex yarn with the body yarn provides anti-slip means on the outer surface of the sole portion which is formed during the formation of the sock, thereby eliminating the necessity for a separate step of applying the anti-slip means to the lower surface of the sole of the sock. The formation of the unknit portions of spandex yarn on the outer surface of the sole portion does not distract from the appearance of the hosiery article, and, in fact, provides an attractive stitch pattern thereto.

In the drawings and specification there has been set forth a preferred embodiment of the invention, and although specific terms are employed, they are used in a generic and descriptive sense only and not for purposes of limitation, the scope of the invention being defined in the claims.

That which is claimed is:

1. In a hosiery article for use primarily by bed patients including leg and foot portions knit of body yarn, said foot portion including an upper instep portion and a lower sole portion, the combination therewith of anti-slip means on the outer surface of said sole portion and extending throughout a substantial portion thereof to provide a relatively high frictional surface on said sole portion to minimize slippage of the foot of the patient on the floor, said anti-slip means comprising friction yarn having a substantially higher coefficient of friction than said body yarn, said friction yarn being interknit with said body yarn in spaced-apart areas of said substantial portion of said sole portion and forming unknit portions on the outer surface of said sole portion, said unknit portions extending between said spaced-apart areas in which said friction yarn is interknit with said body yarn, said unknit portions of said friction yarn on the outer surface of said sole portion being adapted to engage the floor and minimize slippage of the foot of the patient.

2. A hosiery article according to claim 1 wherein said friction yarn comprises a bare uncovered spandex yarn.

3. A hosiery article according to claim 1 wherein said unknit portions of said friction yarn on the outer surface of said substantial portion of said sole portion comprises regularly repeated tuck loops of said friction yarn.

4. A hosiery article according to claim 3 wherein said lower sole portion includes courses knit to form adjacent wales, wherein said body yarn forms plain stitch loops in every wale of every other course, and wherein said friction yarn is knit in the remaining courses and alternately forms plain stitches and tuck loops.

5. A hosiery article according to claim 4 wherein said friction yarn forms tuck loops extending over two adjacent wales.

6. A hosiery article according to claim 5 wherein said tuck loops of said friction yarn are positioned in the same wales from course to course throughout said lower sole portion.

7. A hosiery article according to claim 5 wherein said tuck loops of said friction yarn in certain courses are staggered in a walewise direction from said tuck loops of said friction yarn in other courses.

8. A hosiery article according to claim 7 wherein said tuck loops of said friction yarn are formed in the same wales in groups of three adjacent courses and wherein said tuck loops of said friction yarn in one group of three adjacent courses are staggered in a walewise direction relative to said tuck loops of said friction yarn in the next group of three adjacent courses.

9. A hosiery article according to claims 6, 7 or 8 wherein said friction yarn forming said tuck loops in said lower sole area is knit in plain stitch loops in every wale throughout said upper instep portion.

10. An anti-embolism stocking for use primarily by bed patients and including an elastic leg portion adapted to apply compressive force to the leg of the wearer, an elastic foot portion knit of body yarn and also adapted to apply compressive force to the foot of the wearer, said foot portion including an upper instep portion and a lower sole portion, and anti-slip means on the outer surface of said sole portion and extending throughout a substantial portion thereof to provide a relatively high frictional surface on said sole portion to minimize slippage of the foot of the patient on the floor, said anti-slip means comprising friction yarn having a substantially higher coefficient of friction than said body yarn, said friction yarn being interknit with said body yarn in spaced-apart areas of said substantial portion of said sole portion and forming unknit portions on the outer surface of said sole portion, said unknit portions extending between said spaced-apart areas in which said friction yarn is interknit with said body yarn, said unknit portions of said friction yarn on the outer surface of said sole portion being adapted to engage the floor and minimize slippage of the foot of the patient.

11. An anti-embolism stocking according to claim 10 wherein said friction yarn comprises a bare uncovered spandex yarn.

12. An anti-embolism stocking according to claim 10 wherein said unknit portions of said friction yarn on the outer surface of said substantial portion of said sole portion comprises regularly repeated tuck loops of said friction yarn.

13. An anti-embolism stocking according to claim 12 wherein said lower sole portion includes courses knit to form adjacent wales, wherein said body yarn forms plain stitch loops in every wale of every other course, and wherein said friction yarn is knit in the remaining courses and alternately forms plain stitches and tuck loops.

14. An anti-embolism stocking according to claim 13 wherein said friction yarn forms tuck loops extending over two adjacent wales.

15. A low-cut slipper type sock for use primarily by bed patients including a short leg portion with a supporting cuff adapted to engage the ankle of the wearer, an elastic foot portion knit of body yarn, said foot portion including an upper instep portion and a lower sole portion, and anti-slip means on the outer surface of said sole portion and extending throughout a substantial portion thereof to provide a relatively high frictional surface on said sole portion to minimize slippage of the foot of the patient on the floor, said anti-slip means comprising friction yarn having a substantially higher coefficient of friction than said body yarn, said friction yarn being interknit with said body yarn in spaced-apart areas of said substantial portion of said sole portion and forming unknit portions on the outer surface of said sole portion, said unknit portions extending between said spaced-apart areas in which said friction yarn is interknit with said body yarn, said unknit portions of said friction yarn on the outer surface of said sole portion being adapted to engage the floor and minimize slippage of the foot of the patient.

16. A low-cut slipper type sock according to claim 15 including a heel pocket and a fish mouth toe closure, and wherein said unknit portions of said friction yarn also extend throughout the outer surface of the lower portion of said fish mouth toe closure.

17. A low-cut slipper type sock according to claim 15 wherein said friction yarn comprises a bare uncovered spandex yarn.

18. A low-cut slipper type sock according to claim 15 wherein said unknit portions of said friction yarn on the outer surface of said substantial portion of said sole portion comprises regularly repeated tuck loops of said friction yarn.

19. A low-cut slipper type sock according to claim 18 wherein said lower sole portion includes courses knit to form adjacent wales, wherein said body yarn forms plain stitch loops in every wale of every other course, and wherein said friction yarn is knit in the remaining courses and alternately forms plain stitches and tuck loops.

20. A low-cut slipper type sock according to claim 19 wherein said friction yarn forms tuck loops extending over two adjacent wales.

21. A low-cut slipper type sock according to claim 20 wherein said tuck loops of said friction yarn are positioned in the same wales from course to course throughout said lower sole portion.

22. A method of producing a hosiery article for use primarily by bed patients including leg and foot portions with the foot portion including an upper instep portion and a lower sole portion, said method comprising the steps of knitting the leg portion with a body yarn while forming successive courses of stitch loops in adjacent wales, knitting the foot portion with the body yarn while interknitting a friction yarn having a substantially higher coefficient of friction than said body yarn in spaced-apart areas of a substantial portion of the sole portion and forming unknit portions on the inner surface of said sole portion, and everting the hosiery article to position the unknit portions of said friction yarn on the outer surface of said sole portion so that the unknit portions of the friction yarn are positioned to engage the floor and minimize slippage of the foot of the patient when the hosiery article is positioned on the foot.

23. A method of producing a hosiery article according to claim 22 wherein said unknit portions of said friction yarn are formed by forming tuck loops between the spaced-apart areas where said friction yarn and said body yarn are interknit.

* * * * *